United States Patent
Topping et al.

(12) 
(10) Patent No.: US 6,245,326 B1
(45) Date of Patent: Jun. 12, 2001

(54) HEALTH SUPPLEMENT

(75) Inventors: David Topping, Glenelg North; Alexander James Jozsa, Burwood East; Patanjali Rao, Wantirna, all of (AU)

(73) Assignee: Sigma Pharmaceuticals Pty. Ltd., Clayton (AU)

( * ) Notice: Subject to any disclaimer, the term of this patent is extended or adjusted under 35 U.S.C. 154(b) by 0 days.

(21) Appl. No.: 09/474,134

(22) Filed: Dec. 29, 1999

Related U.S. Application Data

(63) Continuation of application No. PCT/AU98/00503, filed on Jun. 30, 1998.

(30) Foreign Application Priority Data

Jun. 30, 1997 (AU) .......................................... 7631

(51) Int. Cl.⁷ .................................................. A61K 31/74
(52) U.S. Cl. .......................................................... 424/78.01
(58) Field of Search ..................... 424/78.07; 514/53–61; 536/42, 56

(56) References Cited

U.S. PATENT DOCUMENTS

| 4,784,861 | 11/1988 | Gori ........................................ 426/74 |
| 5,227,248 | 7/1993 | Wullschleger et al. .............. 426/549 |
| 5,232,698 | 8/1993 | Hord ................................. 424/195.1 |
| 5,234,916 | 8/1993 | Hord ....................................... 517/57 |
| 5,382,443 | 1/1995 | Kincaid et al. ...................... 426/620 |
| 5,422,101 | 6/1995 | Daggy et al. ..................... 424/78.01 |

FOREIGN PATENT DOCUMENTS

| 17139/83 | 1/1984 | (AU) . |
| 44924/89 | 5/1990 | (AU) . |
| 66817/90 | 5/1991 | (AU) . |
| 37306/93 | 10/1993 | (AU) . |
| 50516/93 | 1/1994 | (AU) . |
| 45520/93 | 3/1994 | (AU) . |
| 57352/94 | 7/1994 | (AU) . |
| WO 93/13801 | 7/1993 | (WO) . |
| WO 93/17586 | 9/1993 | (WO) . |
| WO 93/17588 | 9/1993 | (WO) . |
| WO 93/17590 | 9/1993 | (WO) . |
| WO 95/13801 | 5/1995 | (WO) . |
| WO 97/03685 | 2/1997 | (WO) . |
| WO 97/06808 | 2/1997 | (WO) . |

*Primary Examiner*—Jose' G. Dees
*Assistant Examiner*—Konata M. George
(74) *Attorney, Agent, or Firm*—Foley & Lardner

(57) ABSTRACT

A composition for improving bowel health in humans including a combined cholesterol reducer and faecal bulk promoter such as psyllium in combination with a promoter of short chain fatty acids (in particular butyric acid) in the colon which also has faecal bulking properties. High amylose starch is a particular example of a useful faecal bulk promoter which also promotes the formation of short chain fatty acids.

22 Claims, No Drawings

HEALTH SUPPLEMENT

This application is a Continuation of PCT/AU98/00503, filed Jun. 30, 1998.

FIELD OF THE INVENTION

This invention relates to compositions and methods for improving health, particularly compositions which improve bowel health, have laxative properties and promote lowering of blood cholesterol levels.

BACKGROUND OF THE INVENTION

There are many different laxatives for improving bowel comfort through the easier passage of stool. Some of these rely on pharmacological components to improve Taxation through stimulating contraction of the muscles of the colon wall. However, while these irritant agents improve Taxation, they do little to improve the health of the bowel in the short or long term.

The optimal laxatives are those which rely on alternatives to such pharmacological ingredients. Generally, these are based around compositions which contain bulking agents in the form of indigestible polysaccharides ("dietary fibre" and "resistant starch") and, as such, promote faecal bulk. It is known that increased intake of dietary fibre and, to a lesser extent, resistant starch increase stool mass and the frequency of defecation in humans. Many fibre-rich preparations relieve simple constipation promptly and effectively and they can be of value in the prevention and management of diverticular disease. In addition to increased faccal bulk, some of the bulking agents produce benefits through the production of short chain fatty acids (SCFA). These acids are produced by the fermentation of dietary carbohydrates by the colonic microflora. It appears that the provision of SCFA to the colonic mucosa is essential for the maintenance of its integrity and for the normal functioning of the organ. Also, SCFA appear to be essential for the prevention of non-infectious large bowel disease and their supply may be especially significant for the distal colon (where the incidence of these diseases is greater). Production of SCFA appears to predominate in the caecum and proximal colon where the supply of substrate is high. As digesta passes along the colon, SCFA availability falls through exhaustion of substrate coupled with absorption and utilisation of the acids.

Recent studies have shown that the major SCFA, specifically acetate, propionate and butyrate (but possibly others including succinate and formate) may have a number of effects. Collectively, they lower digesta pH-an effect which is thought to lower the risk of colonic cancer through limiting the absorption of toxic compounds such as amines. The three major SCFA stimulate fluid and electrolyte transport and so reduce the risk of diarrhoea. They promote the flow of blood to the colon so that tissue perfusion may be improved and also they stimulate muscular contraction. The major SCFA seem to stimulate colonocyte proliferation and butyrate is thought to promote a normal cell phenotype. The latter acid is a major metabolic fuel for colonocytes and a number of in vitro studies have suggested that it lowers the risk of colonic cancer by promoting DNA repair and inhibiting the growth of transformed cells. Thus butyrate would appear to be the most beneficial of the SCFA. Other studies have demonstrated a direct therapeutic benefit in that instillation into the colon of humans with ulcerative colitis leads to a prompt remission of the condition.

In addition to lowering the risk of non-infectious disease, dietary fibre and resistant starch may be of benefit to colonic health by stimulating the growth of non-pathogenic bacteria. Thus the conditions favouring SCFA production and in particular butyrate will have an additional advantage in lowering disease risk.

Whilst some of the bulking agents increase SCFA, this does not necessarily occur with all such agents. For example, one of the commonly used bulking agents, namely psyllium, can act to reduce the level of SCFA in the colon. However, because psyllium also has the effect of promoting a reduction of cholesterol in the blood stream, it is a preferred bulking agent in situations where blood cholesterol reduction is of importance.

Other bulking agents which may have a cholesterol lowering effect include guar gum, pectin, konjac, modified carbohydrates including hydroxy propyl cellulose, hydroxy propyl methyl cellulose, carboxy methyl cellulose and methyl cellulose. Again, whilst they may have a blood cholesterol lowering effect they generally do not act to significantly improve SCFA levels in the colon and in particular may suppress levels of butyrate the most important of the SCFA.

Ideally, the most desirable laxative compositions should be able to reduce blood cholesterol and promote presence of SCFA including butyrate in the colon whilst providing the bulk necessary for healthy laxation.

DISCLOSURE OF THE INVENTION

In one aspect the invention provides a composition suitable for ingestion by animals, the composition including a bulk forming material, a cholesterol reducer and a fatty acid promoter, the relative proportions and nature of the ingredients in the composition being chosen to promote faecal bulk, an increase of butyric acid in the colon and a reduction of plasma low density lipoprotein (cholesterol). The composition may be particularly suitable for human treatment.

For the purposes of this specification bulk forming material refers to any ingestable material which significantly assists formation of faecal bulk in the colon by resisting digestion in the small intestine so that it may be utilised by the flora in the colon to provide a fermentable substrate with the resultant flora contributing to faecal mass. Also the water retentitive properties of the faecal mass may be increased.

The composition will include at least two different components, although it is to be understood that a single component may provide more than one of the attributes of the composition. For example the bulk forming material may also act to reduce levels of cholesterol or it may promote the presence of butyric acid in the colon. There may be more than one bulk forming material one of which may promote butyric acid formation and another promotes cholesterol lowering.

Preferably the composition is water soluble and/or forms a dispersion or suspension in water. Suitably it may be in the form of a drink mix. Alternatively the composition may take the form of a fine powder or tablets. It may be in a form suitable for incorporation into foods such as cakes or biscuits.

Suitably the bulk forming material will form 20% to 60% by weight of the composition, more preferably 30% to 50% by weight and most preferably about 40% by weight.

Preferably the bulk forming material includes fibrous material. It is preferably soluble or dispersable in water. Suitably one or more of any other substances, and most preferably all substances which are included in the composition are soluble or dispersable in water as well.

The bulk forming material may suitably include hydrophilic colloids. The bulk forming material may be fibrous. The fibrous material may be a hydrophilic colloid. The fibrous material may include and/or be derived from, agar, plantago seed (psyllium), kelp (alginates), plant gums such as tragacanth, chondrus, guar and karaya (sterculia), cellulose including synthetic cellulose derivatives such as carboxy methyl cellulose, hydroxyl propyl methyl cellulose and methyl cellulose, pectin and malt extract and any pharmaceutically acceptable combination and/or derivatives of these. Most suitably the bulk forming material comprises psyllium. Suitable derivatives of any of the foregoing fibrous materials may include derivatives having compounds such as fatty acid covalently bonded thereto by a bond hydrolysable in the colon to give or promote free fatty acid in the colon, particularly butyric acid. Other such derivatives could include ones based upon 5 amino salicylic acid.

Where the bulk forming material includes psyllium it may suitably comprise psyllium husk derived from psyllium seeds obtained from plants of the plantago genus. The psyllium husk is obtained from the seed coat of the seeds and is preferably reduced to a particle size which facilitates dispersion in water. Generally speaking it is preferred that the majority of psyllium husk particles will pass through a 60 mesh screen.

Another preferred form of bulk forming material is a starch or starch derivatives which resists digestion in the small intestine. It may include a maize starch. Preferably the starch is one having a high amylose content. Suitably, the starch includes at least 50%, more preferably at least 70% by weight amylose. Amylose is generally associated with a high level of dietary fibre and/or resistant starch content.

The starch source may include Hi-maize, an unmodified food grade maize marketed by Starch Australasia Ltd. A suitable type of maize having a high amylose content is described in Australia patent No. 660560 in the name of Goodman Fielder Ltd.

Preferably the composition includes both a high amylose starch and a hydrophilic colloid such as psyllium both being bulk forming materials. The psyllium has the additional characteristic of being able to lower blood cholesterol whilst the high amylose starch promotes the formation of SCFA and particularly butyric acid, in the colon.

The term fatty acid promoter as used herein denotes any substance (apart from psyllium) which acts to enhance the level of butyric acid in the bowel. It may be a bulk forming material. It may be material which facilitates formation of butyric acid in the colon in the presence of a bulk forming material which can act as a fermentable substrate.

The fatty acid promoter may be a starch source and/or a material which includes a fatty acid, particularly butyric acid covalently bonded to a carrier (FACBC) by a bond hydrolyzable in the colon to release free fatty acid. Suitably the fatty acid promoter promotes the release and/or formation of fatty acids, especially butyric acid and optionally other fatty acid in the colon. Preferably the fatty acid is SCFA. The SCFA may be acetate, propionate or butyrate and/or mixtures thereof.

Compositions containing psyllium alone may lead to increased butyric acid levels. However, the combination of psyllium and fatty acid promoter can lead to an even further increase of butyric acid level.

Where the fatty acid promoter includes butyric acid and optionally other SCFA covalently bonded to a carrier, the FACBC may be suitably chosen from the range of FACBC's described generally and specifically in Australian patent application No. 81368/94 in the name of Commonwealth Scientific and Industrial Research Organisation. Most preferably the FACBC may be chosen from materials prepared by covalently bonding butyric, andoptionally other SCFA to starch, glucans, pectin, gums, mucillages, cellulose, hemicelluloses, inulin, and oligosaccharides, and/or mixtures thereof.

The fatty acid promoter preferably represents 20% to 60% by weight or preferably 30% to 50% by weight and most preferably about 40% by weight of the composition.

The fatty acid promoter preferably includes a substantial proportion of starch in a form which resists digestion in the small intestine. Most suitably it includes a substantial proportion of high amylose starch.

The fatty acid promoter may include a range of components. For example it may include high amylose starch and FACBC. It may even include one or more subsidiary components which help to create conditions in the bowel for allowing one or more other components in the composition to promote SCFA and particularly butyric acid formation. Thus for example, the high amylose starch which promotes formation of SCFA by fermentation in the colon, may have its effectiveness increased by increasing the number of bifidobacteria in the bowel. Increasing bifidobacteria presence has the useful side effect of reducing the level of less desirable bacteria in the colon, and can thus indirectly lead to increased fermentation.

Thus, inclusion of a bifidobacteria promoting components which can travel through the digestive system to the colon before it is fermented or otherwise substantially altered can significantly increase the SCFA promoting properties of the composition, either by generation of SCFA directly through its own action or fermentation and/or indirectly by improving conditions in the colon for fermentation of other substrates to promote SCFA. Oligofructose is a particularly preferred material for promoting bifidobacteria. It may be included in the compositions in proportions of 0% to 30% more preferably 5% to 25% by weight of the composition.

The cholesterol reducer may be any material which can be ingested and acts to reduce the level of plasma low density lipoprotein. Most suitably it will also include bulk forming material. It may include a fibrous material. It may include a hydrophilic colloid. It may be chosen from the group of hydrophilic colloids and mixtures thereof previously specified as suitable bulk forming materials. Most suitably it may include a major proportion of psyllium.

The components and proportions of components of the composition may be chosen to reduce typical faecal pH. For example, faecal pH may typically be reduced to levels of the order of 5.5 to 7 pH units, more preferably about 6 units after ingestion of a standard dose of the composition on a regular basis. It is thought that low pH is conducive to avoiding cancer.

Preferably, the standard daily composition dosage is of the order of 10 to 30 grams, or more preferably 15 to 25 grams for the composition of the invention.

The composition may include one or more of the optional components which enhance its properties other than its bulking, butyric acid increasing or cholesterol lowering properties. The other components may include an excipient and/or processing aids.

Preferred optional components which aid processing into a granular form are polysaccharides. Suitably the major proportion of polysaccharides are pentasaccharides and/or higher polysaccharides. They may include maltodextrin. The optional components may include maltodextrin, a soluble carrier, filler and product extender. The optional components may comprise 5% to 50% by weight, more preferably 10% to 45% by weight and most preferably 15% to 25% by weight of the composition. The maltodextrin may typically comprise at least 50% more preferably at least 70% by weight of these other optional components.

In order to make the composition more palatable the optional ingredients may include a dispersing agent which assists in suspending and/or dissolving the composition components when mixed with water. Examples of suitable dispersing agents include lecithins and modified lecithins, povidones (polyvinyl/pyrrolidones), sodium lauryl sulphate, polysorbates and silicon dioxide. Typically these may be incorporated in the composition at levels in the range of 0.1% to 5% by weight of the composition.

A particularly preferred composition according to the invention may have added thereto ingredients such as flavouring, sweeteners and/or health supplements such as antioxidants and/or vitamin and/or food derivatives.

Generally speaking the proportions of ingredients in the composition may be specified according to the following preferred weight percentages of the composition:

(i) 40% to 100% more preferably 60% to 100% bulk forming material;

(ii) 25% to 60% more preferably 35% to 50% cholesterol reducer;

(iii) 25% to 60% more preferably 35% to 50% fatty acid promoter; and (iv) 0% to 40% more preferably 10% to 30% of other optional ingredients wherein the cholesterol reducer and/or fatty acid promoter may also comprise part or all of the bulk forming material.

One preferred composition includes the following components:

(i) 25% to 60% more preferably about 40% by weight psyllium;

(ii) 25% to 60% more preferably about 40% by weight high amylose maize starch (e.g. Hi-maize from Starch Australasia Ltd);

(iii) 10% to 30% more preferably about 20% by weight maltodextrin or oligofructose, or a combination thereof.

Another particularly preferred composition has the following components:

(i) 25% to 60% more preferably about 40% by weight psyllium;

(ii) 0% to 60% by weight high amylose maize starch;

(iii) 0% to 60% by weight FACBC;

(iv) 0% to 30% by weight maltodextrin; and (v) 0% to 30% by weight oligofructose wherein the combination of components (ii) and (iii) represent at least 25% by weight of the composition and the combination of components (iv) and (v) represent at least 10% by weight of the composition.

The composition may be administered in the form of a pharmaceutical preparation, in which case it is preferably water soluble and/or readily dispersable in water and/or forms a gel (or a solution of high viscosity in water). To aid dispersion and palatability the composition may include gassing agents such as a mixture of sodium bi-carbonate and citric acid. Alternatively the composition may be administered as a component of a range of foods such as the solid foods, biscuits, bread, cake, confectionary, cereal, or dairy based or oil based preparations.

It may be used to manage and prevent a range of bowel disorders such as constipation, diarrhoeal conditions, irritable bowel syndrome, Crohn's disease, colorectal cancer, diverticular disease and ulcerative colitis. It may also be used to lower the risk of coronary artery disease through lowering of blood cholesterol.

In a further aspect the invention provides a method for promoting bowel health which comprises feeding a subject a composition for promoting bowel health as herein described.

Suitably the composition includes substances which have any one or more of the following effects:

(i) a lowering of plasma LDL cholesterol;

(ii) a lowering of faecal pH in the bowel;

(iii) an increase in total water volume content or stools;

(iv) an increase in faecal SCFA, particularly butyrate excretion; and (v) an increase in faecal bile acid excretion.

Suitably the composition is administered periodically in quantities sufficient to have a significant effect on the measurements of the effect factors identified in clauses (i) to (v) above.

In a further aspect the invention provides a method of formulating a composition as herein described in granular form including the steps of making a mixture containing powdered high amylose starch dissolving maltodextrin and/or oligofructose and optionally other additives in water to give a solution, fluidising the mixture in a fluidised bed, spraying the fluidised mixture with the solution, and drying the sprayed mixture to a moisture content within the range of 5% to 15% more preferably 8% to 10% to produce a granulated material. The psyllium husk may be added to the mixture before or after granulation.

The finished granular product may be allowed to cool after which it may be colour dry blended. Other optional additives can be added by dry blending. Larger lumps in the granular product may be removed by sieving preferably to a mesh size less than 15 mesh more preferably about 24 mesh.

DETAILED DESCRIPTION OF THE PREFERRED EMBODIMENTS

The invention will be described with reference to the following examples which illustrate formulations, experimental procedures and results in relation to preferred compositions.

EXAMPLE 1

Formulation of the Candidate Mixtures

Three test formulas were formulated on a number of criteria which included:

(a) the inclusion of a significant component of "non-fermentable" non-starch polysaccharides (NSP);

(b) the presence of a reasonable component of soluble NSP; and (c) the inclusion of Hi-maize as a source of resistant starch.

The three test formulas were:

Formula 1 40% Hi-maize, 60% Guar

Formula 2 40% Hi-maize, 20% Guar, 40% Psyllium Husk

Formula 3 40% Hi-maize, 20% Guar, 40% Hydroxypropylcellulose (HPC).

EXAMPLE 2

Experimental Design and Methods

Fourteen (14) adolescent male pigs weighing 38 kg (SEM=1) were purchased from a local commercial piggery. They were housed individually in a piggery which had a temperature-controlled environment. They were fed Laucke's Pig Grower Pellets until the start of the experiment when they were fed a purified diet. The latter was formulated from casein, sucrose, cornstarch and safflower oil designed to mimic the Australian diet in total fat, protein and carbohydrate content. The animals were given a commercial (pig) vitamin and mineral supplement to ensure adequate intakes. All animals received 40 g of dietary fibre/day as commercial wheat bran. The dry food ingredients and the vitamin/mineral mixture were mixed in 10 kg batches in a commercial dough mixer and the oil was added. Individual meals of the mixed diet were weighed into freezer bags which were evacuated and sealed and then stored at −20° C. until used.

For feeding, the bags were warmed to room temperature and the contents tipped into the feed bin to which was added the laxative mixture which has been pre-mixed with 500 ml of water. The daily dose was 24.7 g of NSP/animal. The animals were fed twice daily (at 09.00 hr and 15.00 hr, respectively). They were allowed free access to water. This feeding regime was chosen because pilot studies showed that unless the laxatives were premixed thoroughly with water, they became unpalatable on mixing with the starch in the diet.

During the experimental period, the animals were subdivided into 4 groups of three animals with a further group of 2 animals (originally purchased as a reserve). At the start of the experiment, the pigs were transferred to the experimental diet on a Sunday afternoon. Feeding was continued until the Friday afternoon of the same weeks at which time the animals were restored to the Grower Pellets. On the following Sunday they were transferred back to the experimental diets. A Latin square design was used so that at any one time, 3 animals were consuming each of the formulas under test. Two animals also were included in the rotation. The total numbers for each treatment were: Formula 1-12 animals (F1), Formula 2-12 animals (F2) and Formula 3-12 animals (F3).

During the experimental period, all faeces were collected. This was done several times during the day and in the morning and evening. Faeces were weighed fresh and a portion taken for determination of volatile fatty acids (SCFA). Another portion was weighed freeze dried (for moisture). The physical appearance of the stool was gauged and a record kept also of the appearance of the animals.

The animals were weighed once weekly before the 8.30 a.m. feed.

Data are shown as the mean ±SEM for the numbers of observation in parentheses. Statistical evaluation was by analysis of variance incorporating a calculation of least significant difference.

EXAMPLE 3

Results and Interpretation

Quantitative Results

Quantitative results are shown in Tables 1 to 10 hereunder.

TABLE 1

Faecal excretion (g of stool/day) in pigs fed Formulations 1 to 3.

| Day | F1 | F2 | F3 |
|---|---|---|---|
| 1 | 429 | 518 | 434 |
|   | (57) | (43) | (63) |
| 2 | 290 | 304 | 310[a] |
|   | (49) | (50) | (34) |
| 3 | 205 | 178 | 235 |
|   | (16) | (20) | (29) |
| 4 | 192 | 183 | 219 |
|   | (14) | (24) | (18) |
| 5 | 142[a] | 154[b] | 190 |
|   | (23) | (19) | (25) |

Data are shown as the mean ± SEM (in parentheses) for 12 observations (F1, F2, F3). Values on any day sharing a common superscript are significantly different ($P < 0.05$).

TABLE 2

Faecal moisture content (%) in pigs fed Formulations 1 to 3.

| Day | F1 | F2 | F3 |
|---|---|---|---|
| 1 | 66.8 | 70.1 | 68.8 |
|   | (3.9) | (0.7) | (2.1) |
| 2 | 69.6 | 71.0 | 68.0 |
|   | (1.1) | (1.2) | (1.8) |
| 3 | 72.9 | 71.9 | 71.3 |
|   | (0.9) | (1.2) | (1.3) |
| 4 | 69.6 | 71.7 | 72.0 |
|   | (1.4) | (1.0) | (1.3) |
| 5 | 70.0 | 70.4 | 72.2 |
|   | (0.8) | (1.4) | (1.0) |

Data are shown as the mean ± SEM (in parentheses) for 12 observations (F1, F2, F3).

TABLE 3

Concentrations of faecal total volatile fatty acids SCFA (mmol/L) in pigs fed Formulations 1 to 3.

| Day | F1 | F2 | F3 |
|---|---|---|---|
| 1 | 108.5 | 85.9 | 79.6 |
|   | (22.2) | (10.8) | (12.0) |
| 2 | 71.8 | 65.0 | 37.4 |
|   | (12.7) | (6.7) | (6.7) |
| 3 | 55.7 | 62.7 | 64.0 |
|   | (6.2) | (8.3) | (9.2) |
| 4 | 74.3 | 68.4 | 67.6 |
|   | (9.9) | (6.8) | (10.9) |
| 5 | 85.7 | 98.4 | 83.8 |
|   | (9.7) | (13.6) | (13.0) |

Data are shown as the mean ± SEM (in parentheses) for 12 observations (F1, F2, F3).

TABLE 4

Concentrations of faecal acetate (mmol/L) in pigs fed laxative preparations.

| Day | F1 | F2 | F3 |
|---|---|---|---|
| 1 | 67.6 | 51.3 | 48.7 |
|   | (14.4) | (5.6) | (7.0) |
| 2 | 42.4 | 39.2 | 37.4 |
|   | (6.4) | (3.8) | (6.7) |
| 3 | 35.5 | 39.3 | 39.3 |
|   | (4.0) | (5.1) | (5.3) |
| 4 | 47.3 | 43.6 | 42.0 |
|   | (6.4) | (4.0) | (6.4) |
| 5 | 54.8 | 62.4 | 52.0 |
|   | (6.0) | (7.9) | (7.2) |

Data are shown as the mean ± SEM (in parentheses) for 12 observations (F1, F2, F3).

TABLE 5

Concentrations of faecal propionate (mmol/L) in pigs fed laxative preparations.

| Day | F1 | F2 | F3 |
|---|---|---|---|
| 1 | 27.7 | 24.4 | 21.7 |
|   | (5.0) | (5.6) | (3.8) |
| 2 | 18.8 | 18.5 | 18.3 |
|   | (4.4) | (3.8) | (5.5) |
| 3 | 14.1 | 16.5 | 17.0 |
|   | (1.5) | (5.1) | (2.4) |
| 4 | 17.3 | 17.3 | 18.2 |
|   | (1.9) | (4.0) | (3.2) |
| 5 | 19.6 | 24.6 | 21.6 |
|   | (2.4) | (7.9) | (3.8) |

Data are shown as the mean ± SEM (in parentheses) for 12 observations (F1, F2, F3).

TABLE 6

Concentrations of faecal butyrate (mmol/L) in pigs fed Formulations 1 to 3.

| Day | F1 | F2 | F3 |
|---|---|---|---|
| 1 | 13.2 | 10.2 | 91.1 |
|   | (3.5) | (2.0) | (1.2) |
| 2 | 10.5 | 7.3 | 9.4 |
|   | (2.5) | (1.0) | (1.5) |
| 3 | 6.1 | 6.9 | 6.6 |
|   | (0.9) | (1.0) | (1.0) |
| 4 | 9.7 | 7.5 | 8.5 |
|   | (1.9) | (1.3) | (1.2) |
| 5 | 11.2 | 11.4 | 10.1 |
|   | (1.8) | (2.3) | (0.8) |

Data are shown as the mean ± SEM (in parentheses) for 12 observations (F1, F2, F3).

TABLE 7

Faecal excretion of total SCFA (mmol/day) in pigs Forumlations 1 to 3.

| Day | F1 | F2 | F3 |
|---|---|---|---|
| 1 | 39.0 | 32.6 | 26.7 |
|   | (11.2) | (3.8) | (4.8) |
| 2 | 17.4 | 15.7 | 10.1 |
|   | (6.1) | (3.4) | (2.8) |
| 3 | 8.4 | 7.7 | 10.7 |
|   | (1.2) | (0.8) | (1.8) |
| 4 | 8.0 | 8.9 | 10.2 |
|   | (1.1) | (1.3) | (1.9) |
| 5 | 7.7 | 10.3 | 10.4 |
|   | (1.0) | (1.9) | (1.6) |

Data are shown as the mean ± SEM (in parentheses) for 12 observations (F1, F2, F3).

TABLE 8

Faecal excretion of acetate (mmol/day) in pigs fed Formulations 1 to 3.

| Day | F1 | F2 | F3 |
|---|---|---|---|
| 1 | 24.4 | 19.2 | 15.8 |
|   | (7.3) | (1.8) | (2.5) |
| 2 | 9.7 | 9.2 | 6.2 |
|   | (2.8) | (1.7) | (1.4) |
| 3 | 5.4 | 4.8 | 6.6 |
|   | (0.8) | (0.5) | (1.1) |
| 4 | 5.0 | 5.7 | 6.3 |
|   | (0.7) | (0.9) | (1.0) |
| 5 | 4.9 | 6.6 | 6.5 |
|   | (0.6) | (1.2) | (1.0) |

Data are shown as the mean ± SEM (in parentheses) for 12 observations (F1, F2, F3).

TABLE 9

Faecal excretion of propionate (mmol/day) in pigs fed Formulations 1 to 3.

| Day | F1 | F2 | F3 |
|---|---|---|---|
| 1 | 4.6 | 9.4 | 7.8 |
|   | (1.9) | (1.8) | (1.9) |
| 2 | 2.7 | 4.8 | 2.6 |
|   | (1.1) | (1.4) | (0.6) |
| 3 | 2.1 | 2.0 | 2.9 |
|   | (0.3) | (0.2) | (0.5) |
| 4 | 1.9 | 2.3 | 2.7 |
|   | (0.3) | (0.3) | (0.6) |
| 5 | 1.8 | 2.6 | 2.6 |
|   | (0.2) | (0.5) | (0.4) |

Data are shown as the mean ± SEM (in parentheses) for 12 observations (F1, F2, F3).

TABLE 10

Faecal excretion of butyrate (mmol/day) in pigs fed Formulations 1 to 3.

| Day | F1 | F2 | F3 |
|---|---|---|---|
| 1 | 4.6 | 4.0 | 3.1 |
|   | (1.6) | (0.7) | (0.6) |
| 2 | 2.7 | 1.7 | 1.3 |
|   | (1.1) | (0.3) | (0.3) |
| 3 | 0.9 | 0.8 | 1.1 |
|   | (0.1) | (0.1) | (0.5) |
| 4 | 1.0 | 0.9 | 1.1 |
|   | (0.2) | (0.1) | (0.5) |
| 5 | 0.9 | 1.2 | 1.2 |
|   | (0.1) | (0.3) | (0.3) |

Data are shown as the mean ± SEM (in parentheses) for 12 observations (F1, F2, F3).

Solubility Characteristics of the Formulations

Of the new formulae, Formula 3 was the easiest to mix and had the most pleasing appearance. Formula 2 tended to form lumps.

Food Intake and Body Weight Gain

All animals adapted to the experimental diet and the formulations without incident. The food was eaten promptly and all animals showed the same weight gain across the experiment (data not shown) with a final mean body weight of 62±1 kg.

Animal Care Observations

The animals showed no sign of any discomfort either as abdominal pain or reflux during any of the feeding periods. Four (4) pigs showed very mild rectal bleeding. In every instance this occurred as a single incident and was not allied to a specific diet.

Significance

Taken with data on food intake and weight gain, these observations show that none of the formulae had any major adverse reaction. The rectal bleeding has been seen on other occasions and seems to be a nonspecific reaction, possibly to the wheat bran as fibre source.

Stool Appearance

Assessment of stool consistency is a subjective measure and so was carried out by two staff who compared notes and arrived at a common conclusion. Differences between treatments were relatively slight. F1 gave pellet-like stools which were rather dark. F2 and F3 gave soft stools but there was some variation in physical appearance with some formed well and others quite soft.

Of the three formulations F3 appeared to be slightly superior.

Faccal Mass and Water Content

In all cases, faecal excretion declined with time and stabilised at days 4 and 5 of feeding (Table 1). There were no differences in wet weight on days 1–3.

Moisture content was constant across the experiment and was unaffected by treatment (Table 2).

Significance

These data are of great interest in that they show that faecal output was a function of dietary "fibre" intake. However, taken with the data on appearance, it seems that all of the products performed reasonably well although formulation might be a critical factor.

SCFA Concentrations and Output

The concentrations of total and individual SCFA declined from day 1, reaching their lowest point at days 3–4 and then rose on day 5 (Table 3–6). Neither the concentrations nor the proportions of the individual major acids were affected by treatment. In similar fashion, the output of the major acids was unchanged between groups (Table 7–10).

Significance

As with the faecal output data, these results are of great value. They suggest that the inclusion of a laxative mixture raised SCFA in general and propionate and butyrate in particular.

Whilst it has been convenient to describe the invention herein in relation to particularly preferred embodiments, it is to be appreciated that other constructions and arrangements are considered as falling within the scope of the invention. Various modifications, alterations, variations and/or additions to the constructions and arrangements described herein are also considered as filling within the scope and ambit of the present invention.

EXAMPLE 4

Human Feeding Trial 24 men and women with normal bowel function were recruited by public advertisement. The volunteers were asked to consume a low fibre diet with a fibre-free control material, and a mixture of psyllium, Hi-Maize, cellulose and maltodextrins (product SP) in a partially randomised crossover fashion with treatment periods of 2 weeks for each test material. The SP product itself was a granular powder, intended to be ingested as a solution/suspension obtained by stirring the powder with water, fruit juice or other suitable liquid. The SP product had the following composition:

| Component | % | Batch Qty (kg) |
|---|---|---|
| Psyllium husk powder (60 mesh) (*1) | 34.50 | 4.485 |
| Maize Starch (HiMaize) (*1) | 34.50 | 4.485 |
| Maltodextrin (M-100) (*1) | 17.20 | 2.236 |
| Microcrystalline cellulose (PH102) (*1) | 8.60 | 1.118 |
| Aspartame (powder) | 0.30 | 0.039 |
| Citric acid (milled) | 1.50 | 0.195 |
| Orange 55.604/TPO5.72 | 2.00 | 0.260 |
| Lemon 502.138/TPO5.72 | 1.00 | 0.130 |
| Sodium Lauryl sulphate | 0.30 | 0.039 |
| Sunset Yellow (FD&C Yellow 6) | 0.10 | 0.013 |
| Total | 100.00 | 13.000 |

Group 1 subjects (13 subjects) were randomly divided into 2 groups, one of which started on the placebo mix, 2 teaspoons three times daily while the other started on product SP, 2 teaspoons three times daily (22 g or 12 g/day). After 2 weeks each group swapped to the alternate product.

Group 2 (11 subjects) began one week after group 1 on control material at a higher dose than group 1 (three teaspoons three times daily). After 2 weeks a proportion of the group was switched to the SP product (three teaspoons three times daily). After 2 weeks the remaining proportion of the group took the SP product.

Subjects collected two days of complete faecal output at the end of each phase. A daily record was kept of faecal number and consistency, and the amount of wind and abdominal pain (if any). Volunteers had two fasting blood tests at the end of each phase. 3 day food records were also kept in each period. A mood rating questionnaire (65 questions) was administered and completed during each arm of the trial.

EXAMPLE 5

Human Feeding Trial—Results a. Subject Characteristics

The mean age, body mass index (BMI; weight/height$^2$), waist:hips ratio, systolic and diastolic blood pressures of the volunteers arc shown in Table 7.1.

b. Dietary Intakes

Analysis of the dietary records showed that the intakes of the major nutrients did not differ between the treatments (Table 7.2). Also the volunteers did adhere to a low-fibre regime with mean intakes in the region of 12–13 g/person/day.

Significance

None of the observed effects between the arms of the experiment was due to differences in the intakes of fibre or the major nutrients.

c. Plasma Lipids

Overall there was no effect of fibre supplementation on total cholesterol, triacylglycerol or HDL cholesterol. However LDL cholesterol was lowered by 5.4% by SP $p<0.02$) compared with the control (Table 7.3). As the food records shows no significant dietary fat changes during the study, it is likely that this fall is an effect of the SP product per se.

d. Mood

No mood changes were apparent over the 6 weeks using a 65 question mood rating scale (Table 7.4). As a group the volunteers were vigorous (42% of maximum score) with very low levels of tension, anger and depression. Only fatigue and confusion achieved moderately positive scores (16% of maximum possible).

Significance

It appears that this group of subjects was a highly motivated one, interested in health and that it would have been difficult to enhance their highly positive responses.

e. Bowel Function

On control material volunteers had 16.1 bowel actions/week; with SP product this increased further to 19.6. Overall, diet had a significant effect on the number of stools (p<0.01) with the contrast between control and SP the only significant contrast (p=0.02). The SP fibre supplement significantly softened the faeces (p=0.001). There was a strong effect of diet order with only a minor change in rating of stool softless when the control material was taken second. However if the control material was used first then SP was rated as producing a markedly softer stool. There were no significant changes in abdominal pain, distension or wind production, although there was a trend for more wind with the SP (p=0.09).

Significance

Softening of the stool is to be expected with increased intake of NSP and the relative efficacy of SP is consistent with greater fermentation as some of the effect will be through a greater bacterial mass. Greater wind is to be expected under these circumstances as gas evolution is a sine qua non of large bowel bacterial metabolism of dietary NSP and RS.

f. Faccal Variables

Faecal variables are shown in Table 7.5. As expected, the stool mass was increased by the consumption of SP. However, this was significant only against the mean of control (Table 7.5). The most striking result was the capacity of SP to lower stool pH. As anticipated, the moisture content was increased by SP. Total water volume was increased significantly by SP against the control.

Significance

The increase in stool mass is consistent with greater intake or NSP and RS while the lowering of pH with SP consumption accords with greater fermentation. This lowering is regarded beneficial as it renders alkaline toxic compounds (such as amines) less available.

g. Faecal SCFA

Faecal SCFA concentrations were higher with SP. This difference was highly significant for total SCFA and also for the major acids (acetate, propionate and butyrate). SCFA excretion (the product of concentration and faecal water mass) also was significantly higher for total acids, acetate and butyrate with SP.

Significance

These data add another point of difference between SP and the control. The concentration of total and individual VFA was higher with SP than with the control. The higher VFA values with SP accord with the pH data and show that butyrate (a major fuel for colonocytes) was present in higher concentration and total amount in the faeces.

h. Faecal Bile Acid Excretion

Concentrations of total individual bile acids in faecal water did not differ between treatments due to a high degree of variability between subjects. Excretion of total bile acids was significantly higher with SP against the control (Table 7.8). Most of the bile acids recovered in water were secondary acids and the only significant difference was in deoxycholate. Excretion of this acid was significantly higher with SP when compared with the control.

Significance

The higher excretion of bile acids with SP is consistent with one of the likely mechanisms whereby NSP lower plasma cholesterol. Secondary bile acids are thought to be tumour promoters and the lack of any difference in concentration is of interest. Of particular value is the fact that both bile acid and butyrate excretion were raised by SP. The consensus has been that, with increasing faecal bile acid excretion, faecal butyrate should fall. This seems to be the first time that not only has a fall not occurred but that, actually, butyrate has risen.

EXAMPLE 6

Attributes of the SP Product

The following attributes and points of difference may be ascribed to SP relative to the control:

Low content of sucrose.

Contains fibre and resistant starch

Lowering of LDL cholesterol.

Greater faecal bulk, stool frequency and softening.

Lower faecal pH.

Higher faecal SCFA concentrations.

Greater faecal SCFA excretion.

Higher faecal butyrate excretion.

Greater faecal bile acid excretion.

No lowering in faecal butyrate despite greater faecal bile acid excretion.

EXAMPLE 7

Human Feeding Trial—Table of Results

TABLE 7.1

SUBJECT CHARACTERISTICS

| Gender | Age (years) | Body Mass Index | Systolic Blood Pressure (mm Hg) | Diastolic Blood Pressure (mm Hg) | Waist:Hips Ratio |
|---|---|---|---|---|---|
| Female | 46.4 ± 10.4 | 26.5 ± 3.9 | 128.6 ± 21 | 74.8 ± 9.5 | 0.79 ± 0.05 |
| Male | 47.0 ± 10.4 | 27.1 ± 3.5 | 129.6 ± 9.2 | 82.4 ± 9.6 | 0.91 ± 0.08 |

TABLE 7.2

DIETARY INTAKES

| Treatment | Protein | Fat | Carbohydrate (g/person/day) | Fibre |
|---|---|---|---|---|
| Control | 87.6 ± 18.7 | 64.7 ± 23.0 | 204.8 ± 51.3 | 11.8 ± 4.7 |
| SP | 87.4 ± 23.6 | 64.7 ± 23.6 | 222.3 ± 68.2 | 12.0 ± 2.7 |

TABLE 7.3

PLASMA LIPID CONCENTRATIONS

| Treatment | Total Cholesterol | Triacylglycerol | HDL Cholesterol | LDL Cholesterol |
|---|---|---|---|---|
| Control | 5.06 ± 0.62 | 1.29 ± 0.59 | 1.28 ± 0.37 | 3.18 ± 0.51 |
| SP | 4.94 ± 0.67 | 1.36 ± 0.59 | 1.27 ± 0.36 | 3.01 ± 0.49* |

TABLE 7.3-continued

PLASMA LIPID CONCENTRATIONS

| Treatment | Total Cholesterol | Triacylglycerol | HDL Cholesterol | LDL Cholesterol |
|---|---|---|---|---|

*Statistics suggest this amount of reduction of LDL cholesterol in comparison with the control should reduce the risk of coronary artery disease by 12%.

TABLE 7.4

MOOD INDICES

| Treatment | Anger | Anxiety | Confusion | Depression |
|---|---|---|---|---|
| Control | 2.58 ± 3.11 | 1.32 ± 3.70 | 4.90 ± 2.58 | 13.42 ± 5.60 |
| SP | 2.52 ± 2.63 | 1.00 ± 3.58 | 4.47 ± 1.90 | 13.63 ± 6.13 |

TABLE 7.5

FAECAL VARIABLES

| Treatment | Faecal Weight (g/2 days) | pH | Moisture (%) | Water (mL/2 days) |
|---|---|---|---|---|
| Control | 226 ± 37 | 6.72 ± 0.08 | 74.5 ± 1.6 | 1.75 ± 33 |
| SP | 372 ± 33 | 6.50 ± 0.08 | 79.5 ± 1.3 | 300 ± 29 |

TABLE 7.6

FAECAL SCFA CONCENTRATIONS

| Treatment | Acetate | Propionate (mmol/L) | Butyrate (mmol/L) | Total |
|---|---|---|---|---|
| Control | 65 ± 7 | 20 ± 2 | 18 ± 3 | 113 ± 12 |
| SP | 81 ± 7 | 29 ± 3 | 25 ± 3 | 145 ± 12 |

TABLE 7.7

FAECAL SCFA EXCRETION

| Treatment | Acetate | Propionate (mmol/2 days) | Butyrate (mmol/2 days) | Total |
|---|---|---|---|---|
| Control | 11.9 ± 2.4 | 3.9 ± 0.9 | 3.3 ± 0.8 | 23.6 ± 5.9 |
| SP | 25.7 ± 3.7 | 9.0 ± 1.4 | 7.0 ± 1.7 | 45.0 ± 6.5 |

TABLE 7.8

FAECAL BILE ACID EXCRETION

| Treatment | Litho | Deoxy | Cheno | Hyodeoxy | Ursodeoxy | Cholate | Total |
|---|---|---|---|---|---|---|---|
| Control | 2 ± 2 | 20 ± 24 | 1 ± 3 | 1 ± 3 | 1 ± 3 | 2 ± 7 | 28 ± 35 |
| SP | 3 ± 3 | 46 ± 46 | 2 ± 3 | 2 ± 3 | 1 ± 2 | 1 ± 3 | 54 ± 52 |

Abbreviations are: litho, lithocholate; cheno, chenodeoxycholate; hyodeoxy, hyodeoxycholate; and, urso, ursodeoxycholate.

EXAMPLE 9

Formulation and Manufacturing Process
Formulation

The following formulation was prepared according to the three manufacturing processes described below:

| COMPONENTS | % BY WEIGHT |
|---|---|
| Psyllium husk powder | 37.4% |
| HiMaize (Resistant Starch) | 37.4% |
| Maltodextrin | 18.2% |
| Citric acid | 4.0% |
| Flavour & Colour | 2.6% |
| Aspartame | 0.4% |

Manufacturing Process 1

Psyllium husk powder used in the trials was of 95% purity and a particle size of 60 mesh. HiMaize is a high amylose resistant starch. Psyllium husk powder and HiMaize were added to the bowl of the Glatt WS 60 Fluid Bed Spray Granulator (FBSG). Maltodextrin, citric acid and Aspartame, as per the formulation, were dissolved in filtered water at 45° C. to give a solution of approximately 40–42% solids.

The Psyllium and HiMaize blend was fluidised by air and the maltodextrin/citric acid/aspartame blend sprayed on to the dry fluidised bed. The spray rate was controlled to prevent excessive wetting of the psyllium powder and causing the formation of large lumps/aggregates. The wetting of the psyllium powder caused the resistant starch to stick to the wetted granule which was then dried by the fluidising air to produce an agglomerated powder. The maltodextrin blend also had a coating effect on the starch and psyllium granules and helped produce a free flowing powder that wetted and dispersed very well.

After all the maltodextrin solution was sprayed on, the blend was dried to a final moisture of between 8–10% moisture. The finished product was then allowed to cool and colour dry blended.

To remove some of the larger lumps, the product was sieved through a 24 mesh sieve for final packing. An unflavoured variant (regular) can also be prepared and the difference in the formulation will be that it will not contain any flavouring, sweetener, colour or citric acid.

Manufacturing Process 2

Himaize was added to the bowl of the Glatt WS 60 Fluid Bed Spray Granulator (FBSG). altodextrin, citric acid, Aspartame and colour (Sunset yellow) were dissolved in R/O reverse osmosis) water at 45% to give a solution of approximately 40% solids.

The Himaize was fluidised by air at 75° C. and the maltodextrin/citric acid/Aspartame/colour blend was sprayed on to the fluidised bed. The spray rate was controlled to prevent excessive wetting of the Himaize and causing the formation of large lumps/aggregates. The spray solution had a coating effect on the starch and helped produce a starch with better flow characteristics and also to wet more easily when dispersed in water. After all the solution was sprayed on the Himaize, the agglomerated starch was then dried to a moisture content of between 6–9%. Psyllium husk powder and flavour were then added to the bowl and fluidised to. blend all the ingredients well.

The product was passed through a Quadro Comil mill using a screen with perforations of approximately 1.5 mm to produce a product with a uniform particle size distribution.

Manufacturing Process 3

Psyllium husk powder, Himaize and maltodextrin were added to a Diosna High Speed Mixer Granulator. The blend was then mixed with the impeller and chopper on for the required time. Flavour, colour, sweetener and citric acid were then added to the mix and the blend mixed again for 2 minutes to form the final product mixture.

EXAMPLE 10

Formulation and Manufacturing Process
Formulation

The formulation of example 9 with Isomalt replacing the Maltodextrin was prepared according to the manufacturing process described below:

Psyllium husk powder and Himaize were added to the bowl of a Glatt WS 60 Fluid Bed Spray Granulator. Isomalt, Aspartame, and colour were dissolved in R/O water at 45° C. to give a solution of approximately 40% solids.

The psyllium husk powder and Himaize were fluidised by air maintained at 75° C. and the solution of Isomalt, sweetener and colour was then sprayed on to the fluidised bed. After all the solution was sprayed on, flavour and citric acid were added to the fluidised bed and the mixture dried to a moisture of 6–9% (Note: The agglomerating solution could also include sugar derivatives if desired). The Isomalt solution assisted in the agglomeration of the ingredients and in the formation of a more easily wettable and dispersable granule.

The granules were then passed through a Quadro Comil mill using a screen with perforations of approximately 1.5 mm.

While it has been convenient to describe the invention herein in relation particularly preferred embodiments, it is to be appreciated that other compositions and arrangements are considered as falling within the scope of the invention. Various modifications, alterations, variations, and/or additions to the compositions and arrangements herein are also considered as falling within the scope and ambit of the present invention.

What is claimed is:

1. A composition comprising a bulk forming material, a cholesterol reducer and a fatty acid promoter, wherein a portion of the bulk forming material and the fatty acid promoter comprise high amylose maize starch, the relative proportions and nature of the ingredients in the composition being chosen to promote faecal bulk, an increase of butyric acid in the colon and a reduction of plasma low density lipoprotein when consumed by humans.

2. A composition according to claim 1 comprising the following weight percentages of composition components:
   (i) 40% to 100% bulk forming material;
   (ii) 25% to 60% cholesterol reducer; and
   (iii) 25% to 60% fatty acid promoter.

3. A composition according to claim 2 comprising the following weight percentages of composition components:
   (i) 60% to 100% bulk forming material;
   (ii) 35% to 50% cholesterol reducer; and
   (iii) 35% to 50% fatty acid promoter.

4. A composition according to claim 3 which is soluble or dispersable in water.

5. A composition according to claim 4 wherein the bulk forming material comprises or is derived from a material selected from a group consisting of agar, psyllium, kelp, alginates, plant gums, chondrus, guar and sterculia, cellulose, cellulose derivatives, carboxy methyl cellulose, hydroxy propyl methyl cellulose, methyl cellulose, pectin, malt extract and any pharmaceutically acceptable combination or derivatives of these.

6. A composition according to claim 5 wherein the derivatives of the bulk forming material comprise those having fatty acids covalently bonded to the bulk forming material by a bond hydrolysable in the colon and/or derivatives based upon 5 amino salicylic acid.

7. A composition according to claim 4 wherein the bulk forming material comprises a substantial proportion of psyllium in the form of particles of psyllium husk obtained from the seed coat of the seeds of the plantago genus with the majority of the particles capable of passing through a 60 mesh screen.

8. A composition according to claim 2 wherein the cholesterol reducer comprises a double acting component which has cholesterol reducing and bulk forming properties.

9. A composition according to claim 8 wherein the double acting component is psyllium.

10. A composition according to claim 2 wherein the fatty acid promoter and the bulk forming material comprise a double acting ingredient which has bulk forming and butyric acid promotional properties when present in association with the other components of the composition.

11. A composition according to claim 10 wherein the double acting ingredient is high starch.

12. A composition according to claim 10 wherein the double acting ingredient is a component which comprises butyric acid covalently bonded to a carrier by a bond hydrolysable in the colon to release free butyric acid.

13. A composition according to claim 12 wherein the carrier is chosen from starch, pectins, gums mucillages, cellulose, hemicelluloses, inulin, oligosaccharides or mixtures thereof.

14. A composition according to claim 2 comprising 10% to 30% by weight of other ingredients and the cholesterol reducer and/or fatty acid promoter comprises part or all of the bulk forming material.

15. A composition according to claim 14 wherein the optional ingredients comprise 10% to 30% by weight of maltodextrin and/or oligofructose.

16. A composition according to claim 10 wherein the composition comprises the following components by weight:
   (i) 25% to 60% psyllium;
   (ii) 25% to 60% by weight high amylose maize starch; and
   (iii) 10% to 30% by weight maltodextrin or oligofructose, or a combination thereof.

17. A composition according to claim 10 wherein the composition comprises the following components by weight:
   (i) 25% to 60% psyllium;
   (ii) high amylose maize starch;
   (iii) 0% to 60% of one or more compounds which include butyric acid covalently bonded to a carrier by a bond hydroysable in the colon to release free butyric
   (iv) maltodextrin; and
   (v) 0% to 30% oligofructose wherein components (ii) and (iii) represent at least 25% by weight of the composition and the combination of components (iv) and (v) represent at least 10% by weight of the composition.

18. A composition comprising the following components by weight:
   (i) psyllium husk powder—30% to 40%;
   (ii) maize starch—30% to 40%;
   (iii) maltodextrin—15% to 20%;
   (iv) microcrystalline cellulose—5% to 10%; and
   (v) food acid—0.5% to 4%.

19. A method of formulating a composition according to claim 1 in granular form including the steps of:
  forming a mixture of bulk forming material, cholesterol reducer and a material which promotes the formation of butyric acid in the colon;
  fluidising the mixture in a fluidised bed; and
  spraying the fluidised mixture with water containing dissolved maltodextrin and/or oligofructose.

20. A method of formulating a composition according to claim 1 wherein the mixture contains psyllium and high amylose maize starch.

21. A method of treating human health disorders selected from any one or more of constipation, diarrhoeal conditions, irritable bowel syndrome, Crohn's disease, colorectal cancer, diverticular disease, ulcerative colitis and high blood low density lipoprotein cholesterol, which includes feeding a patient pharmaceutically effective amounts of a composition according to claim 1, periodically.

22. A method of achieving one or more of the following effects in a human patient:
  (i) a lowering of plasma LDL cholesterol;
  (ii) a lowering of faecal pH in the bowel;
  (iii) an increase in total water volume content of steels;
  (iv) an increase in faecal short chain fatty acids, particularly butyrate excretion; and
  (v) an increase in faecal bile acid excretion;
which comprises periodically administering a pharmaceutically effective amount of a composition according to claim 1 for ingestion by the patient.

* * * * *